United States Patent
Bierman

[19]

[11] Patent Number: 5,810,781
[45] Date of Patent: *Sep. 22, 1998

[54] CATHETER FITTING SECUREMENT DEVICE

[75] Inventor: Steven F. Bierman, Del Mar, Calif.

[73] Assignee: Venetec International, Inc., Mission Viejo, Calif.

[*] Notice: This patent issued on a continued prosecution application filed under 37 CFR 1.53(d), and is subject to the twenty year patent term provisions of 35 U.S.C. 154(a)(2).

[21] Appl. No.: 601,527

[22] Filed: Feb. 14, 1996

Related U.S. Application Data

[60] Provisional application No. 60/005,826, Oct. 24, 1995.

[51] Int. Cl.[6] .................................................. A61M 5/32
[52] U.S. Cl. .................. 604/174; 604/180; 128/DIG. 26
[58] Field of Search ..................................... 604/174, 178, 604/179, 180, 283; 128/DIG. 26

[56] References Cited

U.S. PATENT DOCUMENTS

| | | |
|---|---|---|
| D. 273,993 | 5/1984 | Schulte et al. . |
| D. 302,304 | 7/1989 | Kulle et al. . |
| D. 323,390 | 1/1992 | Paine et al. . |
| 2,525,398 | 10/1950 | Collins . |
| 2,533,961 | 12/1950 | Rousseau et al. . |
| 2,707,953 | 5/1955 | Ryan . |
| 3,064,648 | 11/1962 | Bujan . |
| 3,167,072 | 1/1965 | Stone et al. . |
| 3,245,567 | 4/1966 | Knight . |
| 3,394,954 | 7/1968 | Sarns . |
| 3,686,896 | 8/1972 | Rutter . |
| 3,766,915 | 10/1973 | Rychlik . |
| 3,856,020 | 12/1974 | Kovac . |
| 3,900,026 | 8/1975 | Wagner . |
| 3,906,946 | 9/1975 | Nordstrom . |
| 3,920,001 | 11/1975 | Edwards . |
| 3,942,228 | 3/1976 | Buckman et al. . |
| 3,973,565 | 8/1976 | Steer . |
| 4,037,599 | 7/1977 | Raulerson . |
| 4,082,094 | 4/1978 | Dailey . |
| 4,114,618 | 9/1978 | Vargas . |
| 4,116,196 | 9/1978 | Kaplan et al. . |
| 4,123,091 | 10/1978 | Cosentino et al. . |
| 4,129,128 | 12/1978 | McFarlane . |

(List continued on next page.)

FOREIGN PATENT DOCUMENTS

| | | |
|---|---|---|
| 114677 | 8/1984 | European Pat. Off. . |
| 169704 | 1/1986 | European Pat. Off. . |
| 247590A2 | 5/1987 | European Pat. Off. . |
| 263789A1 | 4/1988 | European Pat. Off. . |
| 356683 | 3/1990 | European Pat. Off. . |
| 367549A3 | 5/1990 | European Pat. Off. . |
| 2341297 | 4/1975 | Germany . |
| 2063679 | 6/1981 | United Kingdom . |
| 2086466 | 5/1982 | United Kingdom . |
| 90/05559 | 5/1990 | WIPO . |
| 91/16939 | 11/1991 | WIPO . |
| 92/03070 | 4/1992 | WIPO . |
| 92/03923 | 5/1992 | WIPO . |

OTHER PUBLICATIONS

Arrow "Snap–Lock" Catheter/Syringe Adapter Instructions for Use (publication date unknown).

*Primary Examiner*—Wynn Wood Coggins
*Assistant Examiner*—Bhisma Mehta
*Attorney, Agent, or Firm*—Knobbe, Martens, Olson & Bear, LLP

[57] ABSTRACT

A securement device provides securement attachment of a catheter fitting to the skin of a patient, while allowing convenient disengagement of the catheter fitting from the securement device. This allows a health care provide the ability to replace the fluid supply tubes connected to the fitting without removing the securement device. The securement device also ensures the that components of the catheter fitting remain tightly connected to prevent accidental disengagement of the catheter from the fitting.

22 Claims, 3 Drawing Sheets

U.S. PATENT DOCUMENTS

| | | |
|---|---|---|
| 4,133,312 | 1/1979 | Burd . |
| 4,161,177 | 7/1979 | Fuchs . |
| 4,224,937 | 9/1980 | Gordon . |
| 4,250,880 | 2/1981 | Gordon ..................... 128/DIG. 26 X |
| 4,316,461 | 2/1982 | Marais et al. . |
| 4,324,236 | 4/1982 | Gordon . |
| 4,326,519 | 4/1982 | D'Alo et al. . |
| 4,362,156 | 12/1982 | Feller, Jr. et al. . |
| 4,392,853 | 7/1983 | Muto . |
| 4,397,647 | 8/1983 | Gordon . |
| 4,405,163 | 9/1983 | Voges et al. . |
| 4,449,975 | 5/1984 | Perry . |
| 4,453,933 | 6/1984 | Speaker . |
| 4,474,559 | 10/1984 | Steiger . |
| 4,480,639 | 11/1984 | Peterson et al. . |
| 4,516,968 | 5/1985 | Marshall et al. . |
| 4,585,435 | 4/1986 | Vaillancourt . |
| 4,633,863 | 1/1987 | Filips et al. . |
| 4,660,555 | 4/1987 | Payton ..................... 128/DIG. 26 X |
| 4,711,636 | 12/1987 | Bierman . |
| 4,742,824 | 5/1988 | Payton et al. ............... 128/DIG. 26 X |
| 4,752,292 | 6/1988 | Lopez et al. . |
| 4,792,163 | 12/1988 | Kulle . |
| 4,795,429 | 1/1989 | Feldstein . |
| 4,826,486 | 5/1989 | Palsrok et al. . |
| 4,834,702 | 5/1989 | Rocco . |
| 4,834,716 | 5/1989 | Ogle II . |
| 4,838,858 | 6/1989 | Wortham et al. . |
| 4,852,844 | 8/1989 | Villaveces . |
| 4,857,058 | 8/1989 | Payton . |
| 4,863,432 | 9/1989 | Kvalo . |
| 4,880,412 | 11/1989 | Weiss . |
| 4,897,082 | 1/1990 | Erskine . |
| 4,898,587 | 2/1990 | Mera . |
| 4,919,654 | 4/1990 | Kalt . |
| 4,934,375 | 6/1990 | Cole et al. . |
| 4,955,864 | 9/1990 | Hajduch . |
| 4,966,582 | 10/1990 | Sit et al. . |
| 4,976,700 | 12/1990 | Tollini . |
| 4,981,469 | 1/1991 | Whitehouse et al. . |
| 4,997,421 | 3/1991 | Palsrok et al. . |
| 5,037,397 | 8/1991 | Kalt et al. . |
| 5,084,026 | 1/1992 | Shapiro . |
| 5,192,273 | 3/1993 | Bierman et al. . |
| 5,192,274 | 3/1993 | Bierman . |
| 5,344,414 | 9/1994 | Lopez et al. . |
| 5,354,282 | 10/1994 | Bierman ................................. 604/180 |
| 5,380,293 | 1/1995 | Grant . |
| 5,380,294 | 1/1995 | Persson . |
| 5,380,301 | 1/1995 | Prichard et al. . |
| 5,382,239 | 1/1995 | Orr et al. . |
| 5,382,240 | 1/1995 | Lam . |
| 5,395,344 | 3/1995 | Beisang III et al. . |
| 5,413,562 | 5/1995 | Swauger . |
| 5,456,671 | 10/1995 | Bierman ..................... 128/DIG. 26 X |
| 5,484,425 | 1/1996 | Fischell et al. . |
| 5,496,283 | 3/1996 | Alexander . |
| 5,498,241 | 3/1996 | Fabozzi . |
| 5,520,656 | 5/1996 | Byrd . |
| 5,522,803 | 6/1996 | Teissen-Simony . |
| 5,527,293 | 6/1996 | Zamierowski . |

CATHETER FITTING SECUREMENT DEVICE

RELATED CASE

The present application claims the benefit under 35 U.S.C. § 119(e) of provisional application Ser. No. 60/005,826, filed Oct. 24, 1995.

BACKGROUND OF THE INVENTION

1. Field of the Invention

The present invention relates in general to a catheterization device. In particular, the present invention relates to an anchoring system for a catheter fitting.

2. Description of Related Art

Medical treatment of patients commonly involves the use of percutaneously inserted catheters to direct fluids directly into the bloodstream, a specific organ or an internal location of the patient, or to monitor vital functions of the patient. For instance, epidural catheters are commonly used to direct anesthesia into an epidural space to anesthetize a specific location of the patient.

In practice, fluid (e.g., anesthesia) typically flows through a fluid supply tubing into an indwelling catheter. The catheter and fluid tubing are commonly removably attached by a conventional connector or catheter fitting. One such connector is sold commercially under the mark Snap-Lock™ by Arrow International, Inc., of Reading, Pa.

A health care provider, such as, for example, a nurse or doctor (for ease of description, as used herein the term "health care provider" will refer to health care providers generally and will not be restrictive in meaning), uses adhesive or surgical tape to secure the catheter fitting to the skin of the patient. The application of adhesive tape also helps inhibit movement between the components of the catheter fitting which possibly could loosen and allow the catheter to disconnect from the fitting.

Health care providers also commonly form a safety loop in the tubing so that any tension applied to the tubing does not directly pass to the catheter, but rather is absorbed by the slack of the safety loop. The health care provider typically loosely tapes the loop to the skin of the patient.

This entire taping procedure takes several minutes of the valuable time of the health care provider. Furthermore, health care providers commonly remove their gloves when taping because most people find such taping procedures difficult and cumbersome when wearing gloves.

The catheterization process often requires frequent disconnection between the catheter and the fluid supply tube. The catheter tubing is generally replaced every few hours in order to maintain the sterility of the fluid and the free-flow of the fluid through the tubing. A health care provider thus must frequently change the tubing and retape the connection.

A great deal of valuable time is thus used in applying significant amounts of surgical tape to the catheter fitting. The frequent application and removal of surgical tape also commonly results in the excoriation of the skin of the patient in the area of the insertion.

SUMMARY OF THE INVENTION

The securement device of the present invention provides a retainer for securing a catheter fitting, such as that sold under the SNAP-LOCK™ trademark by Arrow International, Inc. The securement device is easily anchored to the patient's skin. Once secured, a health care provider can easily insert and remove the catheter fitting from the retainer. The retainer also ensures the that components of the catheter fitting remain tightly connected to prevent accidental disengagement of the catheter from the fitting.

In accordance with one aspect of the present invention, an anchoring system releasably secures a catheter fitting to a patient. The anchoring system comprises a retainer including a first channel which is configured to receive a first tubular portion of the catheter fitting. A second channel of the retainer is also configured to receive a second tubular portion of the catheter fitting. The first and second channels generally extend along a common axis. At least one lateral slot is interposed between the first and second channels. The slot extends in a direction which is generally perpendicular to the common axis. A bottom of the slot has an arcuate shape which generally matches a shape of a collar portion of the catheter fitting.

Another aspect of the invention involves an anchoring system for securing a medical article to the skin of a patient. The medical article includes an elongated tubular body and a radially extending member which projects from the tubular body. The anchoring system comprises a retainer including first and second channel portions which extend about an axis, each channel portion generally having a truncated circular cross-sectional shape sized to surround at least a portion of the medical article through an arc of greater than 180° about the axis. At least one lateral slot extends generally perpendicular to the longitudinal axis between the first and second channel portions. The slot has a thickness substantially equal to the thickness of the radially extending member of the medical article. The first and second channels have a combined longitudinal length sufficient to prevent lateral movement of the medical article with the radially extending member positioned within the lateral slot. A flexible anchor pad has an adhesive bottom surface and a top surface on which the retainer is mounted. The retainer is positioned on the top surface in a manner exposing openings to the channel portions.

In accordance with an additional aspect of the present invention, an anchoring system involves a retainer having a longitudinal channel configured to receive in a snap-fit manner a tubular body of a catheter fitting. The retainer additionally comprises at least one lateral slot sized to receive and to capture a radially extending member of the fitting with the fitting positioned within the longitudinal channel of the retainer. In this manner, the retainer prevents the adaptor from sliding in a longitudinal direction. A flexible anchor pad includes an adhesive bottom surface which is adapted to attach to a patient's skin. The anchor pad supports the retainer.

BRIEF DESCRIPTION OF THE DRAWINGS

These and other features of the invention will now be described with reference to the drawings of a preferred embodiment which is intended to illustrate and not to limit the invention, and in which.

DETAILED DESCRIPTION OF A PREFERRED EMBODIMENT

Figure 1:
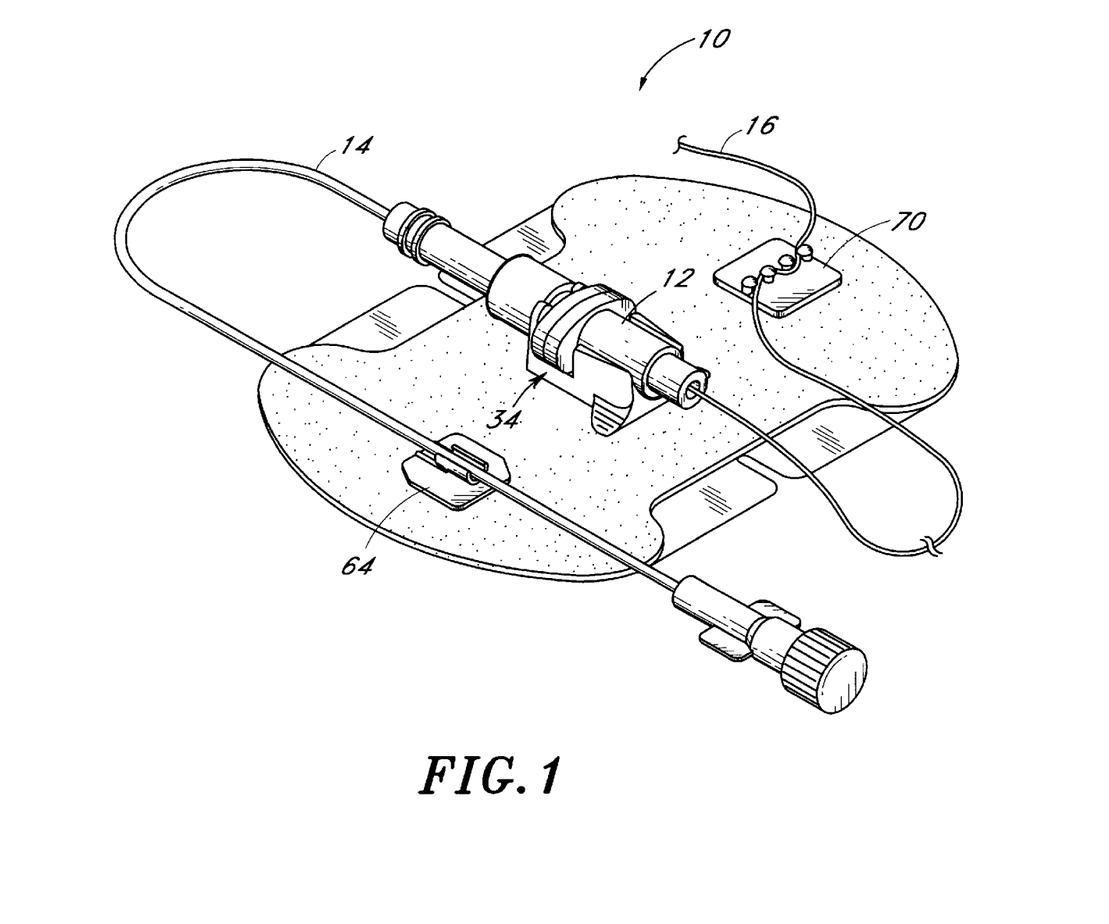
FIG. 1 is a top perspective view of a catheter fitting securement device configured in accordance with a preferred embodiment of the present invention, shown securing an exemplary catheter fitting.

FIG. 1 illustrates a securement device 10 configured in accordance with a preferred embodiment of the present invention. Although the securement device 10 is illustrated in connection with a particular catheter fitting 12, those skilled in the art will readily appreciate that the present securement device 10 can be adapted for use with other types of fittings, connectors and adaptors which are used with catheters, fluid supply and drainage tubes, electrical wires and cables, and the like.

The securement device 10 securely anchors the catheter fitting 12 to the patient without the use of surgical tape. For most catheterization, the securement device 10 is attached to the patient only once. Although a fluid supply tubing 14, which is connected to the fitting 12, may be replaced often for epidural applications, the components of the securement device 10 remain attached to the patient. Thus, surgical tape need not be applied and removed from the patient's skin on multiple occasions.

The general principles of the present securement device 10 are disclosed in copending application Ser. No. 08/223,948, filed Apr. 4, 1994, entitled "Catheter Anchoring System", in the name of Steven F. Bierman, the named inventor of the present application. Application Ser. No. 08/223,948 is hereby incorporated by reference. The present securement device 10 includes additional features which are particularly well suited for catheter fittings and like connectors.

The illustrated catheter fitting 12 is available commercially under the trademark SNAP-LOCK™ from Arrow International of Reading, Pennsylvania. However, before describing the present securement device 10 in detail, the exemplary catheter fitting 12 will first be generally described to assist the reader in understanding the illustrated securement device 10.

Figure 2:
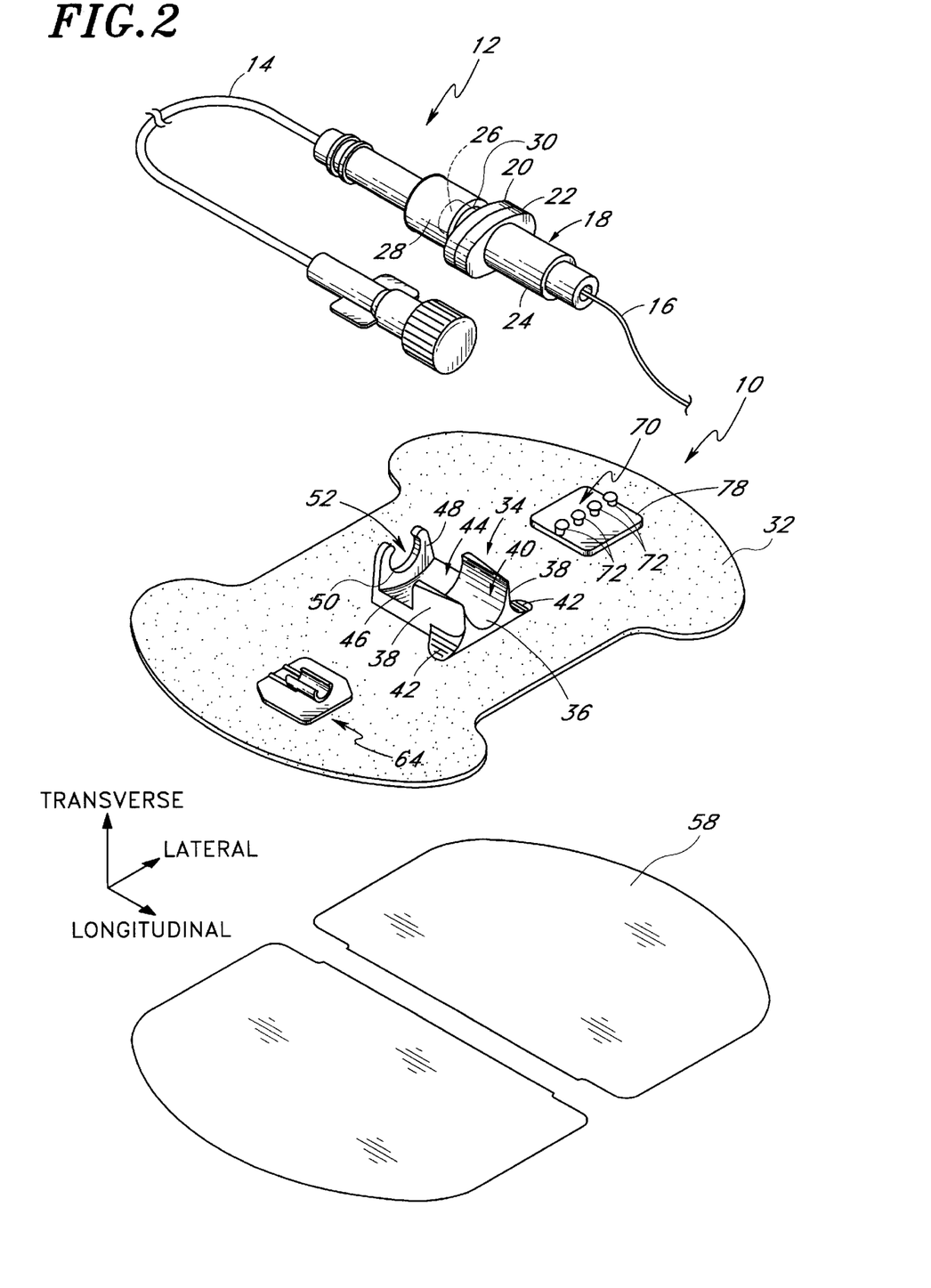
FIG. 2 is an exploded top perspective view of the securement device and catheter fitting illustrated in FIG. 1.

With reference to FIG. 2, the catheter fitting 12 securely connects the tube 14, such as a fluid supply tube, to microbore tubing or catheter 16 (e.g., 18 to 24 gauge). The catheter 16 is releasably connected to the fitting 12 by threading a proximal end of the catheter 16 through a central channel (not shown) within the fitting 12. As used herein, "proximal" and "distal" are used in reference to the proximity of the fluid supply tube 14. The central channel passes through a collet (not shown) of the fitting 12. An outer ring member 18 is slid over the collet section to secure and seal the microbore tubing 16 within the central channel. The ring 18 is slid toward a collar 20 on the fitting body until a collar 22 on the ring 18 contacts the body collar 20. As seen in FIG. 2, the collars 20, 22 generally have identical elliptical shapes and sizes, and rest flush against each other with the ring 18 compressing the collet. Friction between the collet and the ring member 18 tends to maintain the ring member 18 in this position.

The catheter fitting 12 generally presents a cylindrical shape on the distal side of the abutting collars 20, 22. A tubular portion 24 of the ring member 18 principally defines this cylindrical shape.

The catheter fitting 12 also includes a threaded lure-lock connector 26. The connector 26 cooperates with a corresponding connector 28 on the end of the fluid supply tube 14. As understood from FIG. 2, a gap typically exists between the engaged connectors 26, 28 and the proximal side of the fitting collar 20. The exposed portion 30 of the fitting has a tubular shape of a diameter smaller than the diameter of the tubular portion 24 of the ring member 18.

The individual components of the securement device 10 will now be described in detail. To assist in the description of the components of the securement device, a coordinate system has been provided. FIG. 2 illustrates a longitudinal axis, a transverse axis and a lateral axis in relation to the catheter fitting securement device 10. The longitudinal axis extends in a direction generally parallel to an axis of the catheter fitting 12. The lateral axis lies perpendicular to the longitudinal axis generally within the plane of the base of the securement device 10. The transverse axis extends transverse to the longitudinal and lateral axes. Additionally, as used herein, "the longitudinal direction" refers to a direction substantially parallel to the longitudinal axis. "The lateral direction" and "the transverse direction" are in reference to the lateral axis and transverse axis, respectively.

With reference to FIG. 2, the securement device 10 principally includes a flexible anchor pad 32 having an adhesive bottom side which attaches to the skin of a patient when used. The anchor pad 32 can be attached at any number of locations on a patient's body, such as, for example, on the anterior or posterior sides of the patient's torso.

The pad 32 supports a retainer 34. The retainer 34 is configured to receive and secure in place the catheter fitting 12 which interconnects the microbore tubing 16 with the fluid supply tubing 14, as described above. For this purpose, the retainer 34 includes a large central channel 36 interposed between a pair of opposing longitudinal walls 38. The central channel 36 is sized to receive the tubular portion 24 of the fitting ring member 18. The central channel 36 extends along an axis which is generally collinear to the longitudinal axis of the retainer 34.

Figures 4, 6:
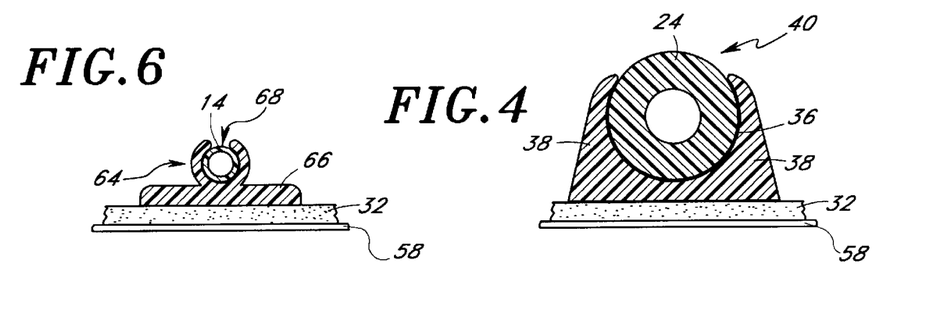
FIG. 4 is a cross-sectional view of a retainer of the securement device shown in FIG. 3 taken along line 4—4 with a portion of the catheter fitting positioned within a channel of the retainer.
FIG. 6 is a cross-sectional view of a tube clip of the securement device of FIG. 3 taken along line 6—6 of FIG. 3.

As best seen in FIGS. 2 and 4, the central channel 36 has a generally circular cross-sectional shape which is truncated at an upper end to form a generally C-shaped channel having an upper opening 40. The central channel 36 has a diameter sized to receive the generally tubular portion 24 of the tube fitting ring 18. In a preferred embodiment, the diameter of the central channel 36 generally matches that of the tubular portion 18 or is slightly larger.

In cross-section, as seen in FIG. 4, the central channel 36 extends through an arc which is greater than 180° about the channel axis such that the lateral width of the opening 40 is less than the diameter of the central channel 36. In an exemplary embodiment, the central channel 36 extends through an arc of about 200° about the channel axis.

The longitudinal walls 38 are substantially identical. The length of each wall 38, measured in the longitudinal direction, is preferably coextensive with the length of the tubular portion 24 of the fitting ring 18.

The walls 38 desirably have a minimum thickness at the top of the channel 36 to allow flexure of the top portions of longitudinal walls 38 away from each other. The retainer 34 further is formed of rigid but flexible material to permit this deflection of the lateral walls 38 when inserting and removing the tubular portion 24 of the catheter fitting 18 from the channel 36. Although the retainer 34 can be formed of any of a wide variety of materials, the retainer 34 desirably is formed of polycarbonate or a like polymer, as discussed below.

Figures 3, 5, 7:
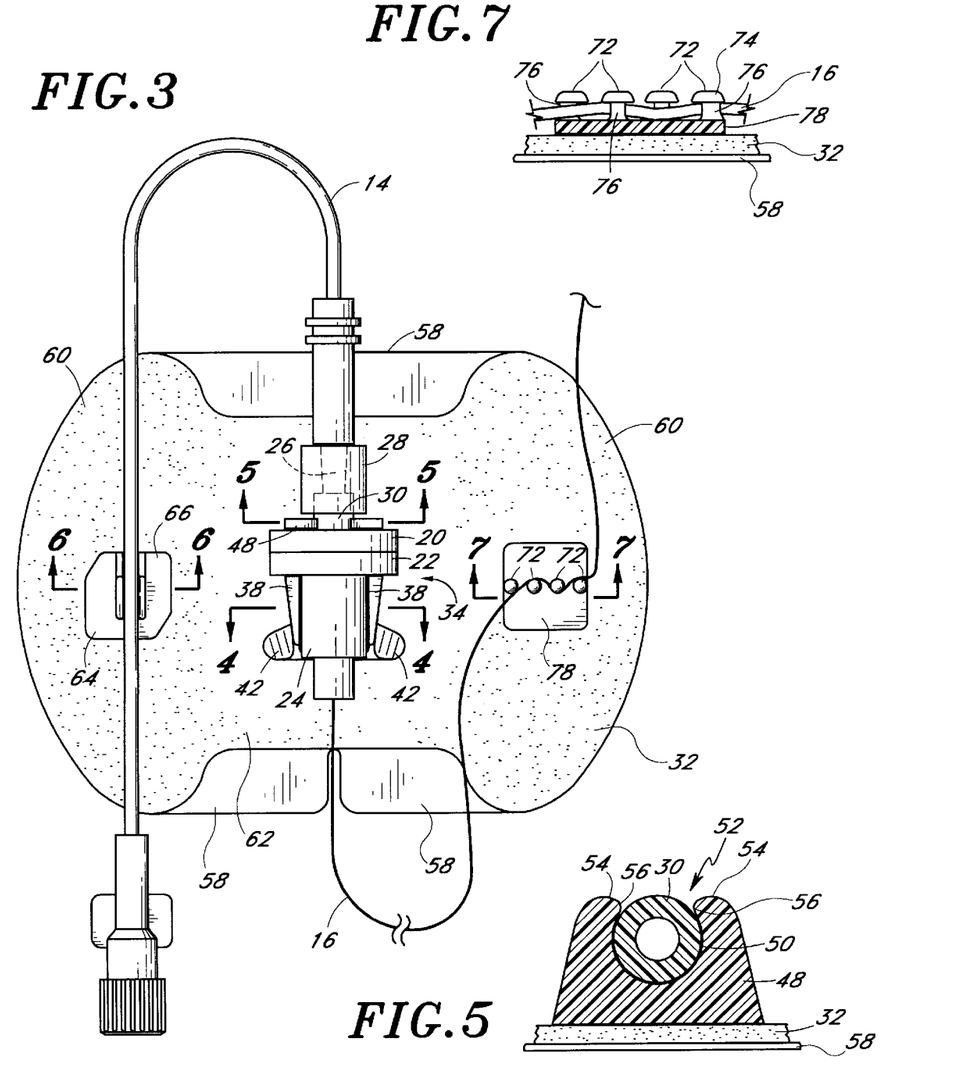
FIG. 3 is a plan view of the securement device and catheter fitting shown in FIG. 1.
FIG. 5 is a cross-sectional view of the retainer of FIG. 3 taken along line 5—5 with a portion of the catheter fitting positioned within an aperture of the retainer.
FIG. 7 is a cross-sectional view of an S-Clip of the securement device of FIG. 3 taken along line 7—7 of FIG. 3.

As best seen in FIG. 3, the walls 38 desirably give the retainer 34 a width in the longitudinal direction which is less than the common maximum width of the fitting collars 20, 22. The distal ends of the longitudinal walls 38 taper in thickness to reduce the width of the retainer 34 at this end.

At the distal end of the retainer 34, a finger platform 42 extends from each wall 38. The platforms 42 have a sufficient size to allow the tips of the health care provider's index finger and thumb to press against the platforms 42. In this manner, the health care provider can press the retainer 34 against the patient when removing the catheter fitting 12 from the retainer 34, as described below.

As best seen in FIG. 2, at least one lateral slot 44 extends through the retainer 34 in a direction that is generally perpendicular to the axis of the retainer 34. The slot 44 is sized to receive the collars 20, 22 of the catheter fitting 12 and includes an arcuate bottom surface 46. The bottom surface 46 is shaped to match the section of the elliptical shaped collars 20, 22 that sit against the bottom surface 46 with the catheter fitting 12 positioned within the retainer 34.

The slot 44 extends through the walls 38 of the retainer 34 such that the ends of the elliptical collars 20, 22 of the catheter fitting 12 are exposed on either side of the retainer 34. That is, the width of the retainer 34 at the location of the slot 44 is less than the major diameter of the elliptical shaped collars 20, 22 of the catheter fitting 12.

The thickness of the slot 44, as measured in the longitudinal direction, generally matches the thickness of the abutting collars 20, 22, measured in the same direction. In this matter, the slot 44 captures a portion of the ends of the collars 20, 22 to prevent longitudinal movement of the catheter fitting 12 within the retainer 34.

As best seen in FIG. 2, the slot 44 has a height, which is measured in the transverse direction, between an upper edge of the longitudinal wall 38 and the bottom 46 of the slot 44. The bottom 44 extends below the central channel 36 in order to receive the portion of the catheter fitting collars 20, 22 that extend below the tubular portion 24 of the ring member 18.

With reference to FIGS. 2 and 3, the retainer 34 includes a slender front wall 48 positioned on the proximal side of the slot 44. The thickness of the wall 48 as measured in the longitudinal direction desirably is less than the gap formed between the catheter fitting collar 20 and the lure-lock connector 28 when engage with the fitting 12.

As best seen in FIGS. 2 and 5, the front wall 48 defines a second channel or aperture 50 which receives the proximal tubular portion 30 of the fitting 12. (In order to differentiate between the proximal and distal channels of the retainer, the following discussion will refer to the channel in the front wall 48 as an aperture; this is done without limiting the invention.) The aperture 50 generally has a circular shape which is truncated at an upper end so as to define an upper opening 52 to the aperture 50. The center of the circular shape of the aperture 50 generally lies on the axis of retainer 34.

The aperture 50 has a diameter sized to receive the proximal tubular portion 30 of the fitting 12. In a preferred embodiment, the diameter of the aperture 50 generally matches that of the proximal tubular portion 30 or is slightly larger.

The aperture 50 desirably extends through an arc which is greater than 180° about the retainer axis such that the lateral width of the opening 52 is less than the diameter of the aperture 50. In an exemplary embodiment, the aperture 50 extends through an arc of about 200° about the retainer axis.

As seen in FIG. 5, the upper edges 54 of the front wall 48 proximate to the aperture opening 52 are rounded and slope toward the opening 52. This configuration helps guide the tubular portion 30 of the catheter fitting 12 into the aperture 50. It also helps deflect the upper ends of the front wall 48 in the lateral direction to allow the health care provider to push the tubular portion 30 into the aperture 50, as described below.

The circular portion of the aperture 50, however, intersects with each sloped upper edge 54 at a generally sharp angle. The resulting distinct transition point 56 inhibits unintentional retraction of the fitting tubular portion 30 from the aperture 50.

The retainer 34 may be constructed in any of a variety of ways which will be well known to one of skill in the art. For instance, the retainer 34 may be integrally molded such as by injection molding or by thermoplasty.

The retainer 34 preferably comprise a durably, flexible material, and more preferably comprise a generally inert, non-toxic material. In a preferred embodiment, the retainer 34 is molded of plastic, such as, for example, polycarbonate, polyvinylchloride, polypropylene, polyurethane, tetrafluoroethylene (e.g., TEFLON®), polytetrafluoroethylene (a.k.a., PTEF), acetal resin (e.g., DELRIN®), chlorotrifluoroethylene (e.g., KEL-F®), nylon or like polymers.

With reference to FIG. 2, the retainer 34 desirably is secured to the anchor pad 32 by means of cyanoacrylate, or other bonding material. The flexible anchor pad 32 comprises a laminate structure formed by an upper paper or other woven or non-woven cloth layer, an inner cellulose foam layer, and a bottom adhesive layer. Alternatively, the flexible anchor pad 32 may comprise an adhesive bottom layer and an upper cellulose foam layer. An upper surface of the foam layer is roughened by corona treating the foam with a low electric charge, as known in the art. The roughened or porous upper surface of the anchor pad 32 improves cyanoacrylate (other types of adhesive or bonding materials) adhesion when attaching the retainer to the anchor pad 32.

A removable paper or plastic backing 58 desirably covers the bottom adhesive surface before use. The backing 58 preferably resists tearing and is divided into a plurality of pieces to ease attachment of the pad 32 to the patient's skin. The backing 58 desirably is split along a center line of the flexible anchor pad 32 in order to expose only half of the adhesive bottom surface at one time. The backing also advantageously extends beyond at least one edge of the anchor pad to ease removal of the backing from the adhesive layer.

In an exemplary embodiment, the laminate structure of the anchor pad 32 is preferably formed by rolling a paper tape, such as a micro-porous rayon tape, available commercially as MICRO-PORE tape from 3M (Item No. 1530), over a medical grade polyvinyl chloride foam tape, such as that available commercially from 3M (Item No. 9777L). The foam tape preferably includes the bottom liner or backing 58. The anchor pad 32 is then stamped out of the laminated sheet of foam and paper. The backing forming the release taps, however, is not severed such that the tabs remain attached. The backing 58 is then cut into two pieces along the center line of the pad between the tabs.

In the illustrated embodiment, as best seen in FIG. 3, the anchor pad 32 includes a pair of lateral wing sections 60 which extend from a narrowed center section 62 of the anchor pad 32. The retainer 34 is attached to the center section 62. As a result, the lateral ends 60 of the anchor pad have more contact area to provide greater stability and adhesion to the patient's skin.

The anchor pad 32 also may include indicia (not shown) which indicates the proper orientation of the anchor pad 32 in reference to the catheterized site. Such indicia can include, for example, arrows, words, icons, or other graphics.

As seen in FIG. 2, the pad 32 may also support a tube clip 64 for retaining a portion of fluid tubing 14. The clip 64, shown in FIGS. 3 and 6, secures the fluid supply tube 14 to form a safety loop, as is known in the art. The tube clip 64 has a plate-like base 66 adhered to or embedded in the anchor pad 32. The tube clip 64 may be located on the pad 34 on either side of the retainer 32.

The clip 64, as best seen in FIG. 6, defines a channel 68 having a generally circular cross-sectional configuration truncated to form an upper orifice. The diameter of the channel 68 is desirably slightly less than that of the fluid supply tube 14 so as to ensure a secure interconnection. The channel 68 receives a portion of the fluid supply tube 14 through the orifice upon application of gentle pressure or by pulling the tubing 14 across and through the orifice of the tube clip 64, as explained below. The clip 64 surrounds a sufficient portion of the tubing 14 with the tubing 14 positioned within the channel 68 to secure and stabilize the held section of tubing 14.

The upper edge of the channel 68 can include tapered ends at the proximal and distal ends of the clip 64. Each tapered end forms a smooth transition between the side edge of the channel 68 and the upper edge, and tapers in lateral width from the side edge toward the center of the tube clip 64. The tapered ends help guide the fluid supply tube 14 into the channel 68 when a health care provider pulls the tube 14 across the clip 64. Thus, the health care provider does not have to pinch the tube 14 to insert it into the clip 64. Also, the health care provider's gloves do not get stuck in the clip 64 when inserting the tube 14, as is typically the case where the health care provider is required to pinch the tube to insert it into the clip 64.

The securement device 10 also can include an S-clip 70 to retain microbore tubing 16. As best seen in FIGS. 2, 3 and 7, the S-clip includes a plurality of retainers 72. Each retainer 72 has a flared head 74 supported by a cylindrical stem 76. The retainers 72 extend upwardly from a base plate 78 and are positioned from one another by a distance slightly greater than the diameter of the microbore tubing 16. The retainers 72 are also positioned such that the spherical heads 74 of the retainers 72 are spaced from one another by a distance slightly less than the diameter of the microbore tubing 16. As best seen in FIG. 1, the retainer heads 74 prevent the microbore tubing 16 from disengaging from the S-clip 70 in the transverse direction once the microbore tubing 16 is snaked between the retainers 72.

An adhesive attaches the base plate 78 of the S-clip 70 to anchor pad 32. Alternatively, the base plate 78 can be attached to the pad 32 by other means known to those of skill in the art (e.g., embedding or otherwise weaving the plate into the base pad).

In use, a health care provider couples the catheter fitting 12 to the proximal end of the catheter 16 through known means and connects a fluid supply tube 14 to the proximal end of the catheter fitting 12. The fluid supply tube 14 communicates with the catheter 16 through the fitting 12 in order to introduce fluids (e.g., anesthesia) to the body canal or cavity in which the catheter distal end indwells.

To secure the catheter fitting 12 to the patient, the health care provider removes the paper backing 58 which initially covers the adhesive bottom surface of the anchor pad 32, and attaches the pad 32 to the patient's skin at a desired location. For epidural application, the pad 32 commonly is attached to the side of the patient's abdomen, to the patient's chest, or to the back of the patient. The health care provider places the bottom layer of the pad 32 against the patient's skin to adhere the anchor pad 32 to the patient. The indicia on the pad 32 preferably point in the direction of the indwelling catheter. Light pressure over the upper layer of the pad 32 assures good adhesion between the pad 32 and the patient's skin. The pad 32, due to its flexibility, conforms to the contours of the topical surface to which the pad adheres.

The health care provider orientates the catheter fitting 12 above the retainer 34 with the collars 20, 22 of the fitting 12 positioned over the lateral slot 44 in the retainer 34. The health care provider then snaps the fitting 12 into the retainer 34. In doing so, the tubular portion 24 of the fitting ring 18 is pressed between the longitudinal walls 38 of the retainer 34 while the proximal tubular portion 30 of the fitting 12 is pressed into the opening 52 of the front wall aperture 50.

As mentioned above, the opening 40 of the channel 36 has a smaller width measured in the lateral direction than the diameter of the tubular portion 24 of the fitting ring 18. Likewise, the opening 52 of the front aperture 50 has a smaller width measured in the lateral direction than the diameter of the proximal tubular portion 30 of the fitting body 12. The longitudinal walls 38 and the lateral side of the front wall 48 thus deflect outwardly in the lateral direction when the fitting 12 is pressed into the retainer 34. The rounded upper edges 54 about the front wall opening 52 ease the insertion of the proximal tubular portion 30 of the fitting 12 into the front aperture 50. Once the tubular portions 24, 30 of the fitting 12 rest within the corresponding channel 36 and aperture 50, the lateral walls 38 and the lateral side of the front wall 48 spring back to snap the fitting 12 into the retainer 34. The walls 38 of the retainer 34 thus prevent unintentional transverse and lateral movement of the fitting 12.

In this position, the collars 20, 22 of the catheter fitting 12 rest in the lateral slot 44. The walls 38, 48 surrounding the slot 44 capture the fitting collars 20, 22 and prevent the longitudinal movement of the fitting 12.

As understood from FIG. 1, the health care provider may also form a safety loop in the fluid supply tubing 14, as known in the art, and secure the safety loop to the patient by inserting a portion of the tubing 14 into the tube clip 64. The safety loop absorbs any tension applied to the fluid supply tube 14 to prevent the fitting 12 and/or the catheter 16 from being pulled.

The health care provider subsequently snakes the microbore tubing 16 through the S-clip 70, as seen in FIGS. 1 and 7, by first pressing the tube between the retainers 72. Light pressure forces the tubing 16 between the retainers 72. The S-clip 70 secures the microbore tube 16 in place and isolates the tube 16 from tension placed on the fitting 12 and/or the fluid supply tube 14.

To remove the catheter fitting 12 from the retainer 34, the health care provider places his or her index finger on one side of the retainer 34 and his or her thumb on the other. The fingers desirably are placed on the platforms 42 of the retainer 34 in order to hold the retainer 34 against the patient. With the other hand, the health care provider grips the end of the fitting collars 20, 22, which extend beyond the side of the retainer 34, with his or her index finger and thumb, and then rotates one end of the collars 20, 22 out of the retainer 34. The opposite side of the slot 44 acts as a fulcrum to allow the health care provider to apply leverage to pull the fitting tubular portions 24, 30 from the corresponding channel 36 and aperture 50 of the retainer 34. This cam-like action forces the fitting 12 from retainer 34 with minimal effort. However, without performing this specific process, it is difficult to remove the fitting 12 from the retainer 34.

Although this invention has been described in terms of a certain preferred embodiment, other embodiments apparent to those of ordinary skill in the art are also within the scope of this invention. Accordingly, the scope of the invention is intended to be defined only by the claims which follow.

What is claimed is:

1. An anchoring system for releasably securing a catheter fitting having a collar portion to a patient, said anchoring system comprising a retainer including first and second portions, a first channel being formed within the first portion and being configured to receive a first tubular portion of the catheter fitting, a second channel being formed within the second portion and being configured to receive a second tubular portion of the catheter fitting, said first and second channels extending along a common axis, and at least one lateral slot interposed between said first and second channels and formed by opposing first and second walls of said first and second portions of the retainer and a bottom surface extending from said first wall to said second wall, said slot extending in a direction perpendicular to said common axis, the bottom surface of said slot having a generally arcuate shape.

2. The anchoring system of claim 1, wherein said first channel is defined by a pair of opposing longitudinal walls, each wall having a finger platform extending laterally from each wall distal to said first channel.

3. The anchoring system of claim 1, wherein at least one of said first and second channels has a generally truncated circular cross-sectional shaped section sized to surround at least a portion of the catheter fitting through an arc of greater than 180° about the common axis.

4. The anchoring system of claim 3, wherein said first channel includes upper sections which slope toward the center of the channel and intersect with the truncated circularly-shaped section of the channel at distinct transition points along edges positioned toward the upper end of the channel on opposing sides of the channel.

5. The anchoring system of claim 1, wherein the slot has a thickness, measured in a direction parallel to a common axis, so dimensioned to substantially match the thickness of the collar portion of a catheter filling measured in a direction parallel to the common axis.

6. The anchoring system of claim 1, wherein side edges of the slot lie at an elevated level relative to a midpoint of the slot between the side edges so as to act as a fulcrum when the collar portion of the catheter fitting is rotated within said lateral slot.

7. The anchoring system of claim 1 additionally comprising a flexible anchor pad having an adhesive bottom surface and a top surface on which said retainer is mounted.

8. The anchoring system of claim 7 additionally comprising a catheter retention device.

9. The anchoring system of claim 8, wherein said catheter retention device is an S-clip including a plurality of upright retainers attached to a base and having retainer heads distal to said base, said retainers spaced from one another by a distance slightly greater than the diameter of the tubular portion of the catheter, and said retainer heads spaced from one another by a distance slightly less than the diameter of the tubular portion of the catheter.

10. The anchoring system of claim 1 additionally comprising a tube clip for securing a portion of a fluid supply tube.

11. A method of removing an adaptor from a retainer of an anchoring system, wherein said retainer has a longitudinal channel for receiving a tubular body of an adaptor, said channel defined by a pair of opposing walls, each wall having a finger platform extending laterally from the wall distal to said channel, and a lateral slot having an arcuate bottom surface extending below said longitudinal channel for receiving a radially extending member of said adaptor with said adaptor positioned within said longitudinal channel of said retain, comprising the steps of:

placing fingertips on said finger platforms and holding said retainer against a patient's body;

gripping said radially extending member of said adaptor with a finger and thumb; and rotating said radially extending member of said adaptor such that a portion of said radially extending member contacts a side of said lateral slot which acts as a fulcrum providing leverage to pull said tubular body of an adaptor out of said longitudinal channel.

12. An anchoring system for releasably securing a catheter to a patient, said anchoring system comprising:

a catheter fitting including a generally tubular body formed at least in part by first and second generally tubular portions which are arranged along a longitudinal axis of the catheter fitting, and a collar extending about the tubular body, said collar having a generally elliptical shape with major and minor diameters; and a retainer including first and second portions, a first channel being formed within the first portion and being configured to receive the first tubular portion of the catheter fitting, a second channel being formed within the second portion and being configured to receive the second tubular portion of the catheter fitting, said first and second channels extending along a common axis, and at least one lateral slot interposed between the first and second channels, said slot being defined at least in part by a pair of generally upstanding side walls, an upper edge of each side wall lying at an elevated level relative to a midpoint of the slot between the side walls and lying below the common axis, and the spacing between the side walls being less than the major diameter of the catheter fitting collar, whereby one of the side edges acts as a fulcrum when the catheter fitting collar is rotated about the common axis within the slot.

13. An anchoring system as in claim 12, wherein major and minor axes of the collar on the catheter fitting lie generally normal to the longitudinal axis of the catheter fitting.

14. An anchoring system as in claim 12, wherein the slot of the retainer extends in a direction generally normal to the common axis.

15. An anchoring system as in claim 12, wherein the retainer first portion includes a pair of opposing longitudinal walls between which the first channel is formed, and each wall has a finger platform that extends outwardly away from the respective wall.

16. An anchoring system as in claim 12, wherein at least one of the first and second channels has a generally truncated circular cross-sectional shape, which is taken in a direction generally normal to the common axis, and is sized to surround at least a portion of the catheter fitting through an arc of greater than 180 degrees about the common axis.

17. An anchoring system as in claim 12, wherein the slot has a width, as measured in a direction parallel to the common axis, that substantially matches the thickness of the catheter fitting collar so as to inhibit movement of the catheter fitting along the common axis when the catheter fitting is inserted into the retainer.

18. An anchoring system for use with a catheter fitting to a patient, the catheter fitting including an elliptically shaped collar with a major axis, said anchoring system comprising:

a retainer including first and second portions, a first channel being formed within the first portion and being configured to receive a first tubular portion of the catheter fitting, a second channel being formed within the second portion and being configured to receive a second tubular portion of the catheter fitting, said first and second channels extending along a common axis, at least a portion of each channel having a generally truncated circular cross-sectional shape, as taken in a direction generally normal to the common axis, which extends through an arc of more than 180 degrees about the common axis, and at least one lateral slot interposed between the first and second channels, said slot being defined at least in part by a pair of generally upstanding side walls that extend generally parallel to the common axis, an upper edge of each side wall lying at an elevated level relative to a midpoint of the slot between the side walls and lying below the common axis, and the spacing between the side walls being so dimensioned to be less than the major diameter of a catheter fitting collar, whereby one of the side edges acts as a fulcrum when the catheter fitting collar is rotated about the common axis within the slot.

19. An anchoring system as in claim 18, wherein the retainer first portion includes a pair of opposing longitudinal walls between which the first channel is formed, and each wall has a finger platform that extends outwardly away from the respective wall.

20. An anchoring system as in claim 18, wherein a curvilinear surface, which extends between the side walls, defines a bottom of the slot.

21. An anchoring system as in claim 18 additionally comprising a flexible anchor pad having an adhesive bottom surface and a top surface on which the retainer is mounted.

22. An anchoring system as in claim 21 additionally comprising a catheter retention device mounted on the top side of the pad next to the retainer.

* * * * *

UNITED STATES PATENT AND TRADEMARK OFFICE
CERTIFICATE OF CORRECTION

PATENT NO. : 5,810,781
DATED : September 22, 1998
INVENTOR(S) : Steven F. Bierman It is certified that error appears in the above-identified patent and that said Letters Patent is hereby corrected as shown below:

In Claim 5, Column 9, Line 51, "catheter filling" should be --catheter fitting--.

Signed and Sealed this

Eighth Day of June, 1999

Attest:

Q. TODD DICKINSON

*Attesting Officer*

*Acting Commissioner of Patents and Trademarks*